United States Patent
Tsuchie et al.

(10) Patent No.: US 6,931,912 B2
(45) Date of Patent: Aug. 23, 2005

(54) ROAD SURFACE FRICTION COEFFICIENT ESTIMATING METHOD, SIGNAL MULTIPLEX TRANSMISSION METHOD AND SIGNAL MULTIPLEX TRANSMISSION DEVICE

(75) Inventors: Shuhei Tsuchie, Kodaira (JP); Yoshinori Imamura, Kodaira (JP); Koji Takao, Kodaira (JP); Masanobu Toyofuku, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 35 days.

(21) Appl. No.: 10/484,005

(22) PCT Filed: Jun. 21, 2002

(86) PCT No.: PCT/JP02/06244

§ 371 (c)(1),
(2), (4) Date: Jan. 16, 2004

(87) PCT Pub. No.: WO03/008246

PCT Pub. Date: Jan. 30, 2003

(65) Prior Publication Data

US 2004/0163454 A1 Aug. 26, 2004

(30) Foreign Application Priority Data

Jul. 19, 2001 (JP) .................................. 2001-219888
Jul. 19, 2001 (JP) .................................. 2001-220381
Jul. 25, 2001 (JP) .................................. 2001-224246

(51) Int. Cl.[7] .......................... E01C 23/00; C01C 23/00
(52) U.S. Cl. ............................................. 73/9; 73/146
(58) Field of Search .................... 73/146, 8, 9, 862.03, 73/862.322, 128, 129

(56) References Cited

U.S. PATENT DOCUMENTS

| | | | | |
|---|---|---|---|---|
| 4,315,426 A | * | 2/1982 | Brandon | 73/9 |
| 5,948,961 A | * | 9/1999 | Asano et al. | 73/9 |
| 6,427,519 B2 | * | 8/2002 | Ueda et al. | 73/9 |
| 6,463,784 B2 | * | 10/2002 | Kashiwagi et al. | 73/9 |
| 6,561,018 B2 | * | 5/2003 | Mancosu et al. | 73/146 |

* cited by examiner

*Primary Examiner*—William Oen
(74) *Attorney, Agent, or Firm*—Oliff & Berridge, PLC (57) ABSTRACT

A method for directly and accurately estimating friction coefficient of a road surface independently from the slip rate is disclosed. The method measures tangential and vertical forces acting on an elastic body 3 of an elastic wheel 1, and calculates the friction coefficient of a road surface based on the measured values of these forces and angular rate of the wheel 1.

11 Claims, 11 Drawing Sheets

ROAD SURFACE FRICTION COEFFICIENT ESTIMATING METHOD, SIGNAL MULTIPLEX TRANSMISSION METHOD AND SIGNAL MULTIPLEX TRANSMISSION DEVICE

TECHNICAL FIELD

The present invention relates to a method for accurately estimating friction coefficient of a road surface which coefficient is indispensable to a control for enhancing a performance of an anti-lock brake system (herein after referred to as an "ABS") or a traction control system.

BACKGROUND

In order to improve a performance of an ABS used in a vehicle, it is considered to be effective to control lock and unlock states in a condition where friction coefficient of a road surface be as large as possible. The friction coefficient of the road surface depends on a slip rate of a tire/wheel assembly under a certain condition of the road surface and therefore the ABS is designed to control lock and unlock states of braking near a slip rate providing the maximum friction coefficient of the road surface.

For this reason, it is a common practice for the conventional ABS to measure a speed of the vehicle and a revolution of the tire/wheel assembly, calculate the slip rate based on the measured values, and automatically control the braking so as the slip rate to fall within a certain range.

However, the method for estimating the frictional coefficient of the road surface from the slip rate has a problem in which the relationship between the slip rate and the friction coefficient of the road surface drastically changes depending on a road surface condition to vary the slip rate corresponding to the optimum friction coefficient of the road surface depending on the road surface condition, so that the optimum friction coefficient of the road surface cannot be obtained from the slip rate alone. Although approaches for solving this problem such as separately estimating the road surface condition as well has been made, satisfactory means have not been proposed yet.

Meanwhile, in connection with this point, an approach for more directly measuring and estimating the friction coefficient of the road surface. Such an approach is known from the disclosure of Japanese Patent Application Opened No. 06-288798A. According to this disclosure, a strain gauge is attached to a suspension suspending the tire/wheel assembly and a strain occurring on this is measured to give a component parallel to the friction force of the road surface or a component perpendicular to the former component of a force acting on the suspension. The means estimate the friction coefficient of the road surface based on these measured values by assuming the values as the friction force of the road surface and the vertical force, respectively.

However, although the method with using a strain gauge is a more direct estimating method as compared with the method of estimating the friction coefficient with the slip rate, there are problems in which the point of measuring the force is far from a vicinity of tire which is the actual point of action of the friction force, so that a measuring result having been influenced by disturbances applied between the point of action of the friction force and the point of measuring the force is obtained, and that the strain gauge is applied on the suspension in which a generated strain is small, and the generated strain is converted to the force, so that its accuracy is not sufficient.

The present invention has been made in view of these problems. It relates to a method for directly estimating friction coefficient of a road surface independently from the slip rate, and its object is to provide a method of real-timely and more accurately estimating the friction coefficient of the road surface by measuring the friction force of the road surface and the vertical force at a region near the tire as well as accurately measuring these forces, and a method and a device of multiplex transmission of signals upon transmitting a measurement signal of a force measured in the vicinity of tire to the ABS displaced on the vehicle body side.

DISCLOSURE OF THE INVENTION

The present invention has been completed to achieve the above-mentioned object, and its gist, constitution and operation will be described below.

(1)

A method of estimating friction coefficient of a road surface according to the present invention calculates, in a tire/wheel assembly having an axle hub, a tire, and a wheel attached to the axial hub to support the tire, tangential and vertical components of a force acting between a section of a transmission path between the axle hub and the tire and the other section of the transmission path, based on measurement values of relative displacements in the tangential and vertical directions, respectively, between the sections of the transmission path, the sections of the transmission path being bounded by an elastic body arranged within the transmission path; and, in calculating the friction coefficient between the tire/wheel assembly and the road surface based on the acting force of these components, an angular rate of the tire/wheel assembly is measured along with measurements of each component of the acting force, and the friction coefficient $\mu$ between the tire/wheel assembly and the road surface is calculated from the equation (1) with the measured tangential force Fb, vertical force N and angular rate $\omega$ as well as the known moment of inertia $I\Omega$ and known effective radius R of the tire/wheel assembly.

$$\mu = (Fb + (I_0/R)d\omega/dt)/N \tag{1}$$

According to the method of estimating the friction coefficient of the road surface, the friction coefficient is not calculated by measuring the slip rate and indirectly determining the friction coefficient of the road surface from the slip rate with a relational expression between the slip rate and the friction coefficient of the road surface, but it is directly calculated by measuring the tangential and vertical component of the force acting on a point of the vehicle. Therefore, the method can accurately and real-timely calculate the friction coefficient which always changes depending on a condition of the road surface, so that an ABS superior in a braking performance can be provided.

Further, it measures a force acting at a point on the vehicle at a point on the tire/wheel assembly being closest to a boundary between the road surface and the assembly at which the friction force actually acts, so that the friction force can be more accurately determined, thereby contributing an improvement of a performance of the ABS.

(2)

Figure 10:
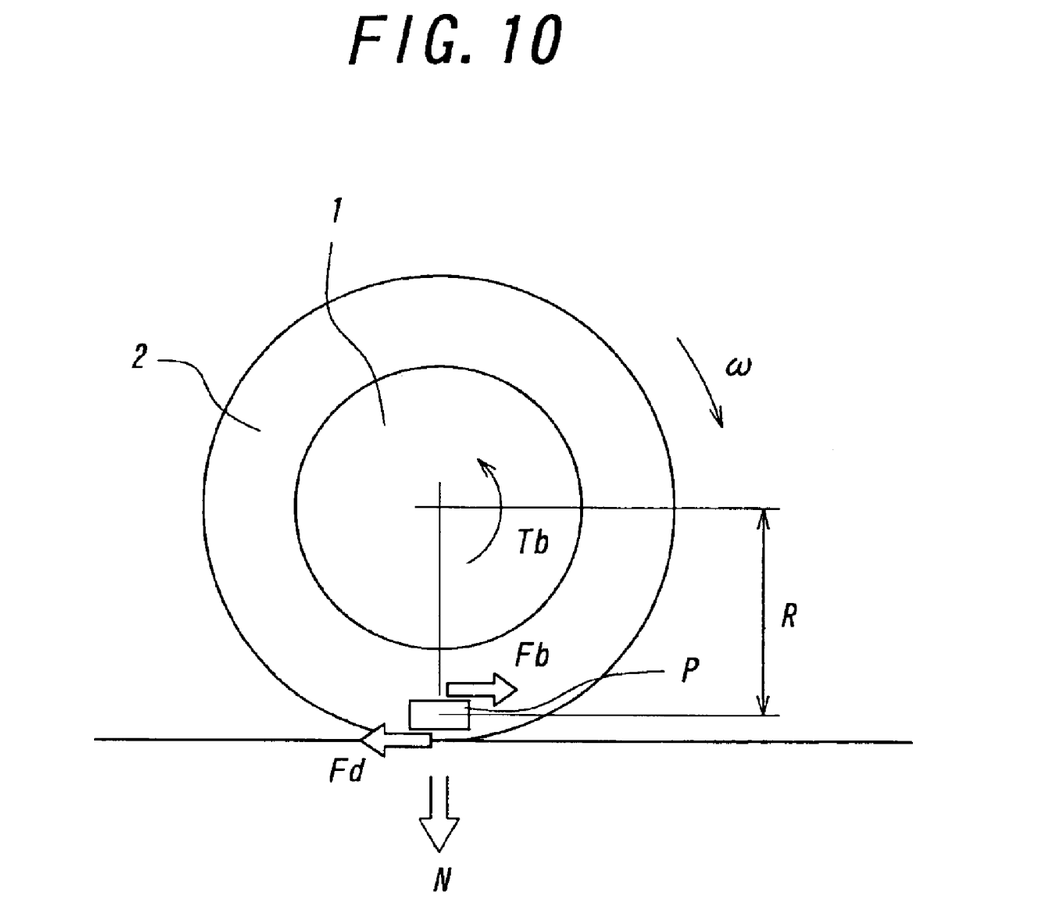
FIG. 10 is a side view of the wheel and the tire.

Moreover, in the present invention, the friction coefficient $\mu$ is calculated by the equation (1), so that it can be estimated with high accuracy. A ground for this equation is discussed with reference to FIG. 10. FIG. 10 is a side view of a wheel 1 and a tire 2 constituting a part of the tire/wheel assembly taken from a side. The tire/wheel assembly rotates at the angular rate $\omega$. When the brake is applied on the tire/wheel assembly, the braking force Fb due to a braking torque Tb, the friction force Fd with respect to the rotation, and a vertical force N act on a part P displaced in a place at a distance of an effective radius R of the tire/wheel assembly from the rotational center. Regarding positive and negative directions of the force, the direction as shown in FIG. 10 by an arrow is defined a positive direction. The dynamic equation of this part can be expressed by the equation (2) with the moment of inertia being $I_0$. The relationship between the braking torque Tb and the braking force Fb can be expressed by the equation (3), and the relationship between the friction force and the vertical force by the equation (4). In the equation (2), when the actual measured value of the tangential force is converted to the braking torque, a radius r of the elastic body from the center of the tire/wheel assembly is assumed to be the same as the effective radius R of the tire/wheel assembly. However, if the radius r is different from the radius R, the measured tangential force may be multiplied by (r/R) to obtain the braking force.

$$I_0 \cdot (d\omega/dt) = R \cdot Fd - Tb \quad (2)$$

$$Tb = R \cdot Fb \quad (3)$$

$$Fd = \mu \cdot N \quad (4)$$

These equation (2), (3), and (4) can derive the equation (1).

(2)

The method of estimating the friction coefficient of the road surface according to the present invention is based on the method described in (1), wherein the tangential relative displacements are summed among each of four pairs of corresponding points comprising four points symmetrically arranged on the section of the transmission path about its axial center and, associated with these points, four corresponding points symmetrically arranged on the other section of the transmission path about its axial center, and the tangential relative displacement of the sections of the transmission path is measured based on the summed value.

By means of the method of estimating the friction coefficient of the road surface, the tangential relative displacements are summed among each of four pairs of corresponding points to calculate the tangential relative displacements of the sections of the transmission path, so that they can be calculated independently from the position of the point of measurement even not in a steady state.

Figure 11:
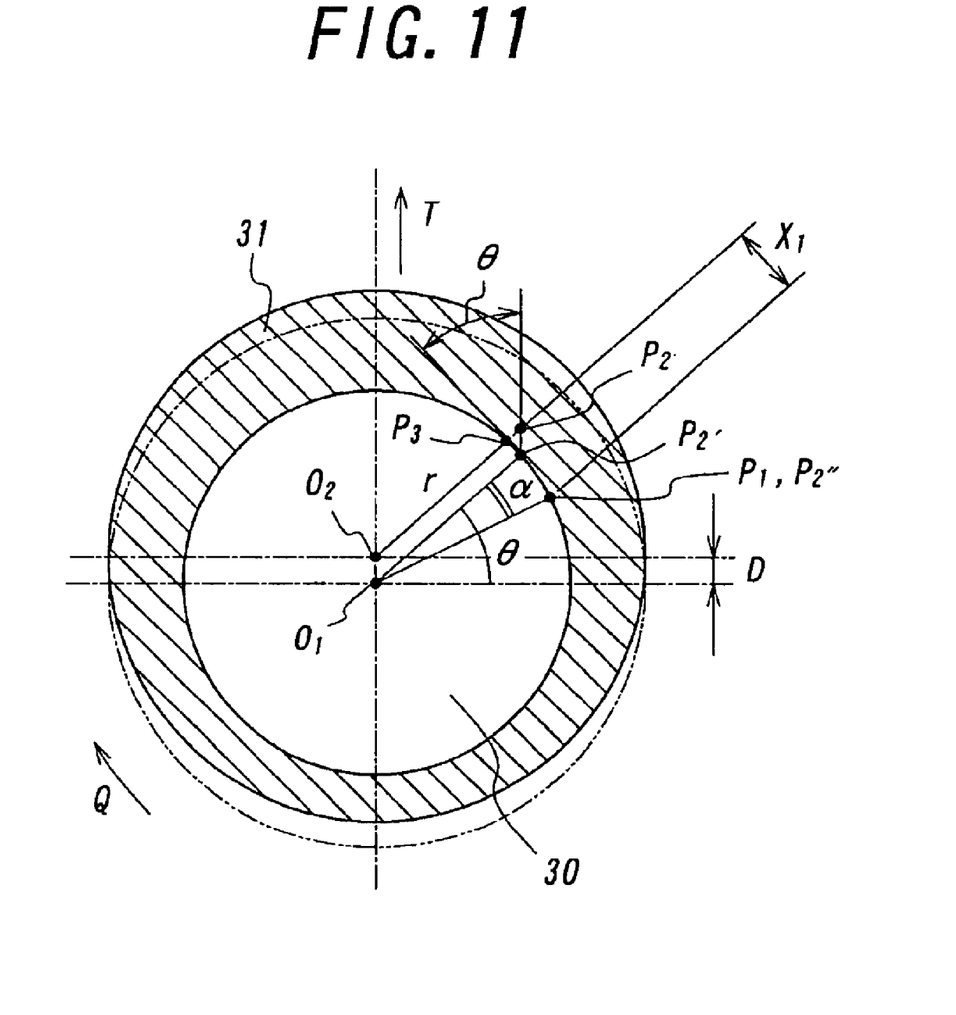
FIG. 11 is a plane view showing the disk and the rim connected thereto.

This is discussed with reference to FIG. 11. FIG. 11 is a plane view showing a disk 30 as an example of one section of the transmission path, and a rim 31 as an example of the other section of the transmission path being bounded by the elastic body. The rim 31 is connected with the disk 30 via the not-shown elastic body. In a state where an eccentric load does not exist, the rim 31 rotates along a rotational direction Q about an axial center identical to an axial center $O_1$ of the disk 30 in conjunction with the disk 30. In FIG. 11, an axial center $O_2$ of the rim 31 is shifted by an amount of eccentricity D due to a vertical reaction force T from the road surface.

In this method, one point $P_1$ of four points of measurement symmetrically displaced about the axial center $O_1$ of the disk 30 and one point $P_2$ of four points of measurement symmetrically displaced about the axial center $O_2$ of the rim 31 are made a pair, and then the tangential components of the displacement of each of the corresponding points $P_1$ and $P_2$ of the pair are measured. Thereafter, the tangential displacements of each of the corresponding points is similarly calculated for the other not-shown three pairs.

All the point of measurement is displaced at a distance of a radius R from each axial center, and rotates about each axial center. The momentary rotation angle is designated as θ.

With respect to the shown pair of the points of measurement, the tangential displacement $X_1$ is calculated. When the disk 30 and the rim 31 are not eccentric and additionally the tangential relative displacement is zero, the point $P_2$ of measurement on the rim 31 agrees with the point $P_1$. When the tangential relative displacement α between the disk 30 and the rim 31 occurs while remaining in the state where no eccentric exists, the point of measurement on the rim 31 is moved to the point $P_2$. The amount of displacement between the corresponding points is equal to the distance between the points $P_1$ and $P_2$, so that the tangential component $X_1$ is equal to the distance between the points $P_1$ and $P_3$, which is expressed by the equation (5) as evidenced by the figure.

$$X_1 = r \cdot \sin(\alpha) + D \cdot \cos(\theta) \quad (5)$$

Although the tangential relative displacement α needs to be calculated, the momentarily-changing relative displacement α between the disk 30 and the rim 31 cannot be calculated based on only one pair of the corresponding points, as is apparent from the equation. It is because the $X_1$ depends on the rotation angle θ of the point of measurement. Consequently, the method of estimating the friction coefficient of the road surface enables a calculation of the tangential relative displacement α independently of the rotation position of a pair of the point of measurement by summing each of the tangential displacements of the four pairs of the corresponding points, and calculating the tangential relative displacement a based on the summed value $Y_1$, as shown in the equation (6).

$$\begin{aligned} Y_1 &= r \cdot \sin(\alpha) + D \cdot \cos(\theta) + \\ &\quad r \cdot \sin(\alpha) + D \cdot \cos(\theta + \pi/2) + \\ &\quad r \cdot \sin(\alpha) + D \cdot \cos(\theta + \pi) + \\ &\quad r \cdot \sin(\alpha) + D \cdot \cos(\theta + 3\pi/2) \\ &= 4r \cdot \sin(\alpha) \end{aligned} \quad (6)$$

(3)

The method of estimating the friction coefficient of the road surface according to the present invention is based on the method described in (1), wherein the radial relative displacements are measured among each of four pairs of corresponding points comprising four points symmetrically arranged on the section of the transmission path about its axial center and, associated with these points, four corresponding points symmetrically arranged on the other section of the transmission path about its axial center, the products of two pairs of the relative displacements in a diagonal relation among the relative displacement are respectively calculated and summed, and the vertical relative displacement of the sections of the transmission path is measured based on the summed value.

By means of this method of estimating the friction coefficient of the road surface, the products of the radial relative displacements of each of the four corresponding points are calculated, two pairs of the corresponding points in a diagonal relation among the relative displacements, the products of the two pairs are summed, and the vertical relative displacement of the above-mentioned section and the other section of the transmission path of the tire/wheel assembly being bounded by the elastic body is decided based on the summed value, so that the displacement can be calculated independently from the position of the point of measurement even not in a steady state.

Figure 12:
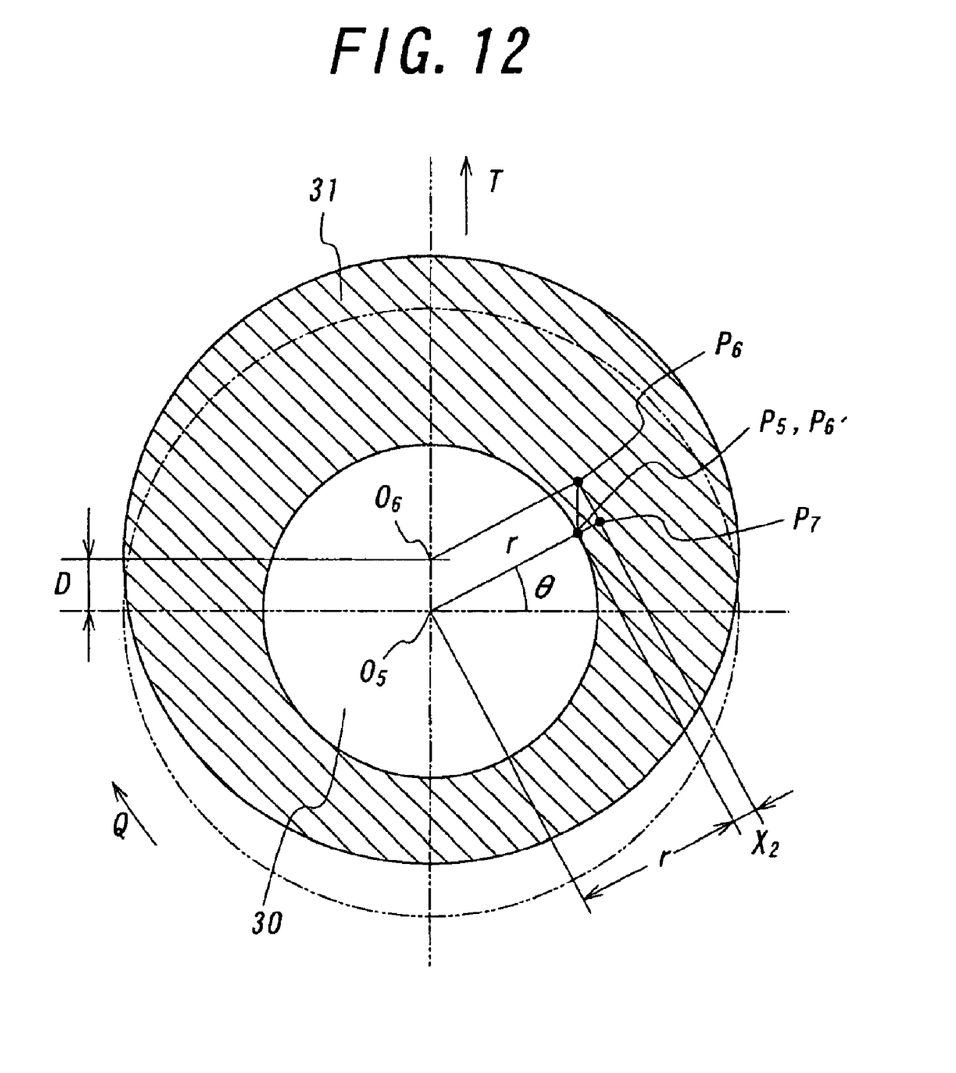
FIG. 12 is a plane view showing the disk and the rim connected thereto.

This is discussed with reference to FIG. 12. FIG. 12 is a planar view showing a disk 30 as an example of one section of the transmission path, and a rim 31 as an example of the other section of the transmission path being bounded by the elastic body. In FIG. 12, the rim 31 is connected to the disk 30 via the not-shown elastic body. In a state where an eccentric load does not exist, the rim 31 rotates along a rotational direction Q about an axial center identical to an axial center $O_5$ of the disk 30 in conjunction with the disk 30. In FIG. 12, an axial center $O_6$ of the rim 31 is shifted by an amount of eccentricity D due to a vertical reaction force T from the road surface.

In this method, one point $P_5$ of four points of measurement symmetrically displaced about the axial center $O_5$ of the disk 30 and one point $P_6$ of four points of measurement symmetrically displaced about the axial center $O_6$ of the rim 31 are made a pair, and then the radial components of the displacement of each of the corresponding points $P_5$ and $P_6$ of the pair are measured. Thereafter, the radial displacements of each of the corresponding points are similarly calculated for the other not-shown three pairs.

Each of the points of measurement rotates about each axial center and its momentary rotation angle is designated as θ.

With respect to the shown pair of the points of measurement, the radial displacement $X_2$ is calculated. When the disk 30 and the rim 31 are not eccentric, the point $P_6'$ of measurement on the rim 31 agrees with the point $P_5$ and the displacement of them is zero.

When an eccentricity occurs in an amount of D, the point of measurement on the rim 31 is moved to the point $P_6$. The amount of displacement between the corresponding points is equal to the distance between the points $P_5$ and $P_6$, so that the tangential component $X_2$ is equal to the distance between the points $P_5$ and $P_7$ which is expressed by the equation (7) as evidenced by the figure.

$$X_2 = D \cdot \sin(\theta) \quad (7)$$

Although the amount of eccentricity D needs to be calculated, the momentarily-changing amount of eccentricity D cannot be calculated based on only one pair of the corresponding points, as is apparent from the equation. It is because the $X_2$ depends on the rotation angle θ of the point of measurement. Consequently, the method of estimating the friction coefficient of the road surface enables a calculation of the amount of eccentricity D independently of the rotation position of a pair of the point of measurement by measuring each of the radial displacements of the four pairs of the corresponding points, calculating the products of the two relative displacements in a diagonal relation among the relative displacements, and calculating the amount of eccentricity D based on the summed value $Y_2$, as shown in the equation (8).

$$Y2 = ((D \cdot \sin(\theta)) \cdot (D \cdot \sin(\theta + \pi))) + \quad (8)$$
$$((D \cdot \sin(\theta + \pi/2)) \cdot (D \cdot \sin(\theta + 3\pi/2)))$$
$$= -2D^2$$

(4)

The method of estimating the friction coefficient of the road surface according to the present invention is based on the method described in any one of (1) to (3), wherein a hall element is used to measure a change in magnetic flux density of the magnetic body, and the tangential or radial relative displacement is detected based on the amount of the change.

By means of this method of estimating the friction coefficient of the road surface, a hall element is used to measure the change in magnetic flux density of the magnetic body to detect the tangential or radial relative displacement, so that the friction coefficient of the road surface can be readily and accurately measured.

(5)

The method of multiplex transmission of signals according to the present invention, upon transmitting signals of the measured values described in any one of (1) to (4) or other signals between the vehicle body side and the rotating tire/wheel assembly side, a composite signal obtained by a voltage/frequency conversion of a plurality of signals is applied to transmitting coil while switching the signals to transmit to a receiving coil by an electromagnetic induction, said plurality of signals having dynamic ranges without overlapping with each other, a plurality of signals obtained by a frequency/voltage conversion of the composite signal received by the receiving coil is processed to generate timing signals with a plurality of given voltage levels as threshold, and said composite signal obtained by the frequency/voltage conversion is sampled according to said timing signals to reproduce a plurality of the original signals.

The above-mentioned measured values described in any one of (1) to (4) are measured by sensors provided on the rotating tire/wheel assembly side. The measured values need to be transmitted at least to an ABS which controls a braking with using the measured values. Therefore, a signal transmittance between the rotating tire/wheel assembly side and the vehicle body side provided with the ABS is needed.

For such a method of transmitting signals between a rotating part and non-rotating part, a method of transmitting signals on carrier waves, so-called a wireless method and a wired method can be used. However, the former has problems in a complicated configuration as well as a large electric power consumption, and the latter, which transmits the signals between the rotating part and the non-rotating part via a mechanical contact point such as a slip ring so that the mechanical contact point extremely deteriorates by wear, has a problem in a maintenance.

As the third method, there has been suggested a method of displacing a transmitting coil on the wheel of the tire side as well as displacing a receiving coil on the vehicle body side to face the transmitting coil, and transmitting a detecting signal from a sensor displaced on the tire side to the receiver coil by the action of electromagnetic induction. However, such a method of transmitting signals by the action of electromagnetic induction is not configured to multiplex a plurality of signals.

By means of the system of multiplex transmission of signals according to the present invention, for example, when the above-mentioned relative displacements are measured while the vehicle is running, and the measured signals are transmitted to the vehicle body side, the detected signals output from a plurality of sensors displaced on the tire side are converted into signals having dynamic ranges without overlapping with each other. Then, as mentioned above, a voltage/frequency conversion is conducted to generate a composite signal which is transmitted from the transmitting coil to the receiving coil by the action of electromagnetic induction. The composite signal received by the receiving coil is subjected to the frequency/voltage conversion, and a plurality of timing signals are generated with a plurality of given voltage level as thresholds. The composite signal obtained by the frequency/voltage conversion is sampled/held according to the timing signals to be able to reproduce a plurality of the original signals.

(6)

The device of multiplex transmission of signals according to the present invention is used for the method of multiplex transmission of signals described in (5), which comprises: a signal-generating circuit for generating a plurality of signals having dynamic ranges without overlapping with each other; a switching circuit for outputting a composite signal by sequentially switching the plurality of signals simultaneously output from the signal-generating circuit at a given cycle; a voltage/frequency conversion circuit for converting the composite signal output from the switching circuit into a composite signal having a frequency corresponding to the voltage; an output circuit for amplifying the composite signal output from the voltage/frequency conversion circuit; a transmitter coil for transmitting the amplified composite signal output from the output circuit; a receiver coil for receiving the composite signal transmitted from the transmitter coil by the action of electromagnetic induction; a frequency/voltage conversion circuit for converting the composite signal received by the receiver coil into a composite signal having an amplitude corresponding to the frequency; a timing signal-generating circuit for generating a plurality of timing signals by processing the composite signal output from the frequency/voltage conversion circuit with a plurality of given voltage levels as thresholds; a plurality of sample/hold circuits for sampling the composite signal output from the frequency/voltage conversion circuit according to the timing signals to reproduce a plurality of the original signals.

By means of the device of multiplex transmission of signals according to the present invention, as is apparent from its configuration, a plurality of the signals described in (5) can be multiplexed and the multiplexed signals can be transmitted between the tire/wheel assembly side and the vehicle body side.

BEST MODE FOR CARRYING OUT THE INVENTION

Figure 1:
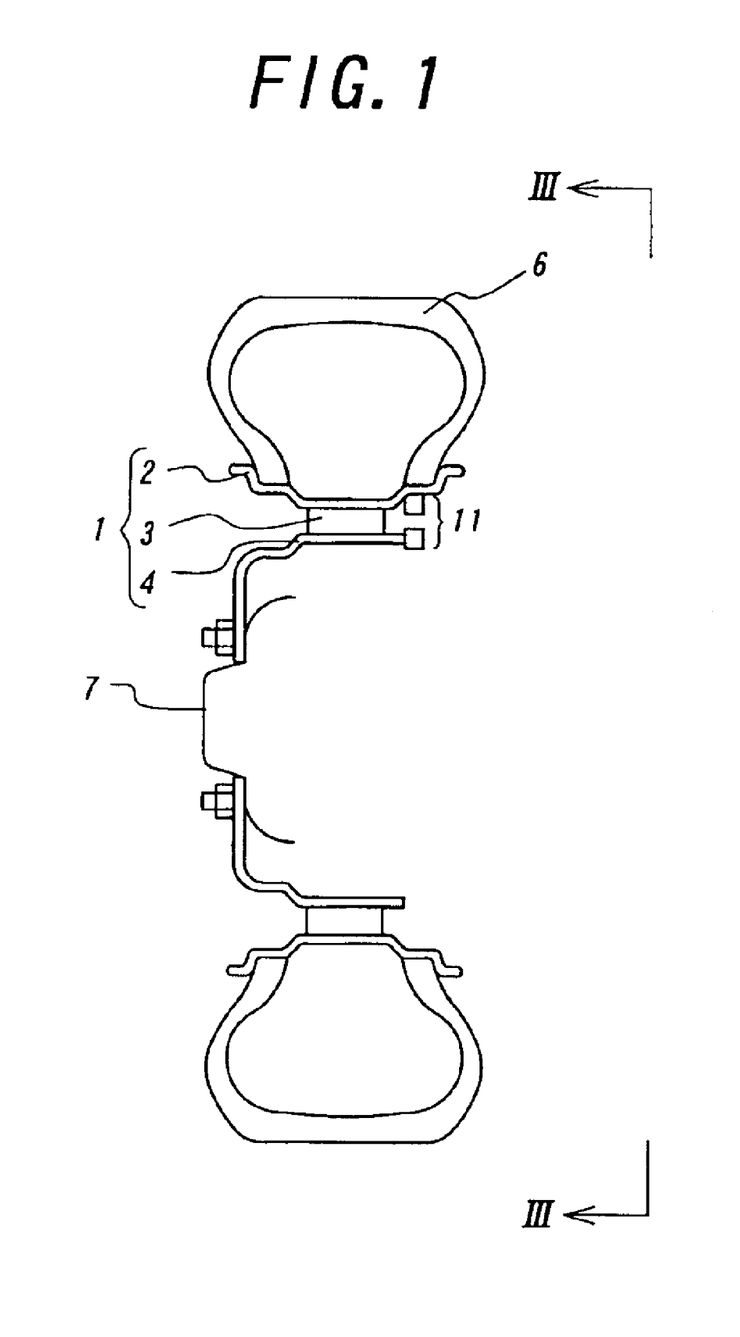
FIG. 1 is a sectional view of the tire/wheel assembly showing an embodiment of the measurement method according to the present invention.

Hereinafter, embodiments of the present invention will be described with reference to FIGS. 1 to 12. FIG. 1 is a sectional view of a wheel 1 showing in a state where the wheel 1 is attached to an axle hub 7 of a vehicle. The wheel 1 is provided with a disk 4 mounted to the axle hub 7, a rim 2 supporting a tire 6, and a rubber-like elastic body 3 connecting the disk 4 with the rim 2 and equipped in a part of a force-transmission path between the axle hub 7 and the tire 6. Being bounded by the rubber-like elastic body 3, one section of the force-transmission path is composed of the disk 4, and the other section of the force-transmission path is composed of the rim 2. A tire/wheel assembly is consist of the axle hub 7, the tire 6 and the wheel 1.

Figure 2:
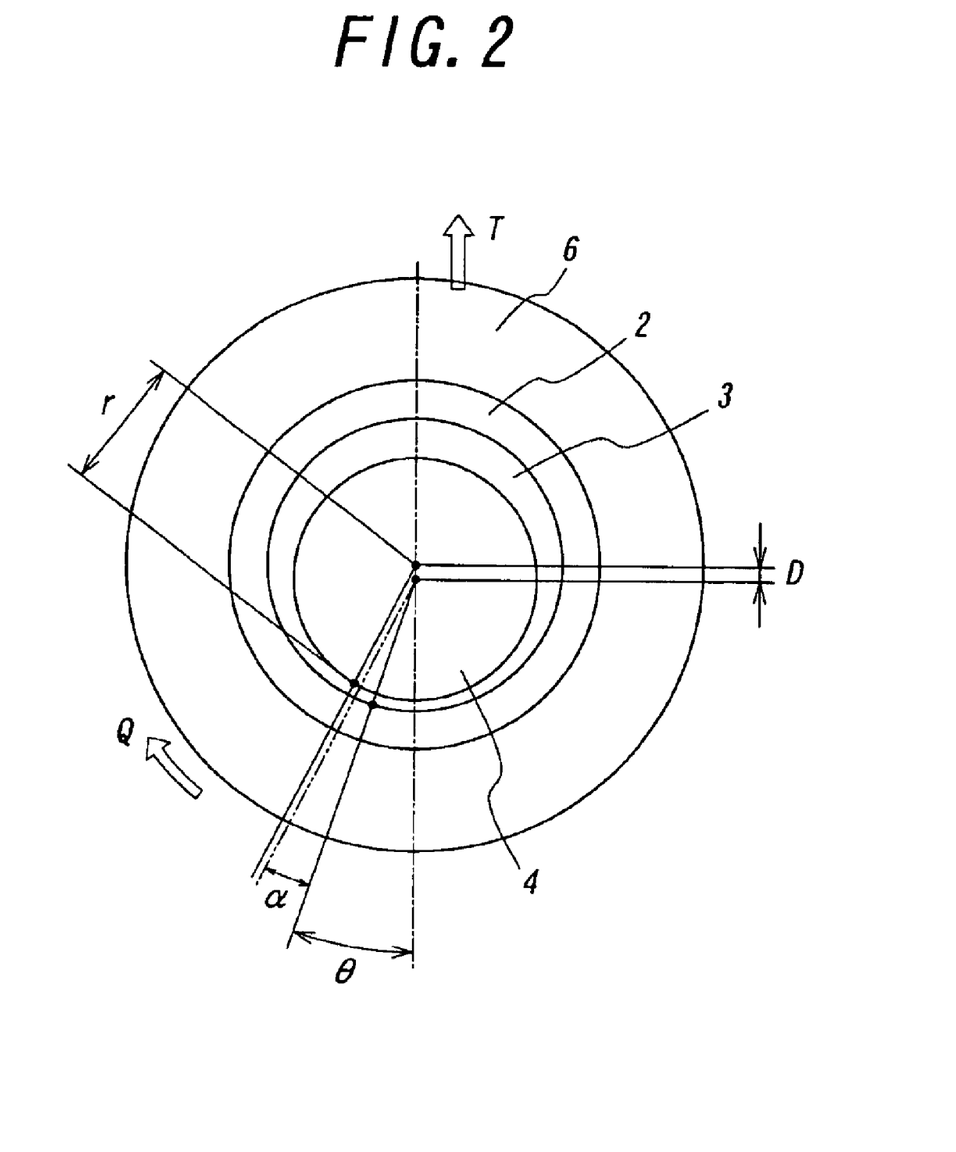
FIG. 2 is a side view of the tire/wheel assembly showing in a state where the tire/wheel assembly is rotating.

FIG. 2 is a side view of the wheel showing in a state where the wheel 1 is mounted on a running vehicle and rolls along the road surface. The rim 2 connected to the disk 4 via the rubber-like elastic body 3 is nearly concentric with the axial line of the disk 4. As the rubber-like elastic body 3 deforms in the vertical direction due to a vertical action of the gravity, the rim 2 is relatively displaced by an amount of eccentricity D in a direction T with respect to the disk 4. The rim 2 is driven via the rubber-like elastic body 3 by the disk 4 to rotate in a rotational direction Q. In this context, the rim 2 torsionally rotates with a tangential relative displacement α with respect to the disk 4 due to an elastic deformation of the rubber-like elastic body 3 in the rotational direction.

Figure 3:
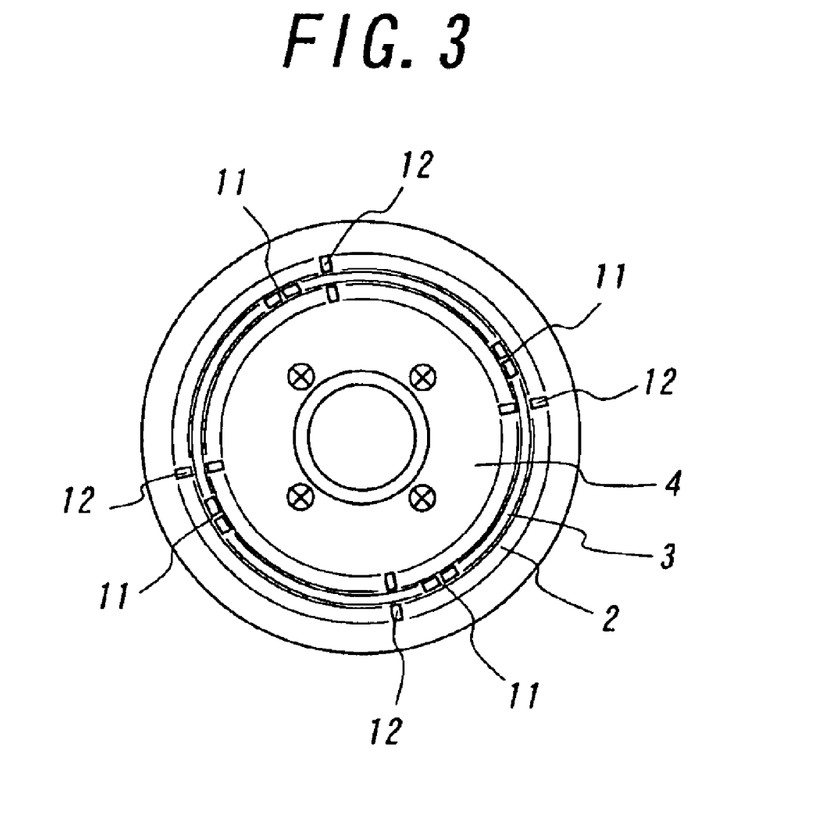
FIG. 3 is a side view of the tire/wheel assembly taken in a direction of the arrows III—III in FIG. 1.

FIG. 3 is a side view of the wheel taken in a direction of the arrows III—III in FIG. 1. As shown in FIG. 3, tangential displacement sensor bodies 11 and vertical displacement sensor bodies 12 are provided at four points on a periphery of the boundary between the rim 2 and disk 4 of the wheel 1.

Figure 4:
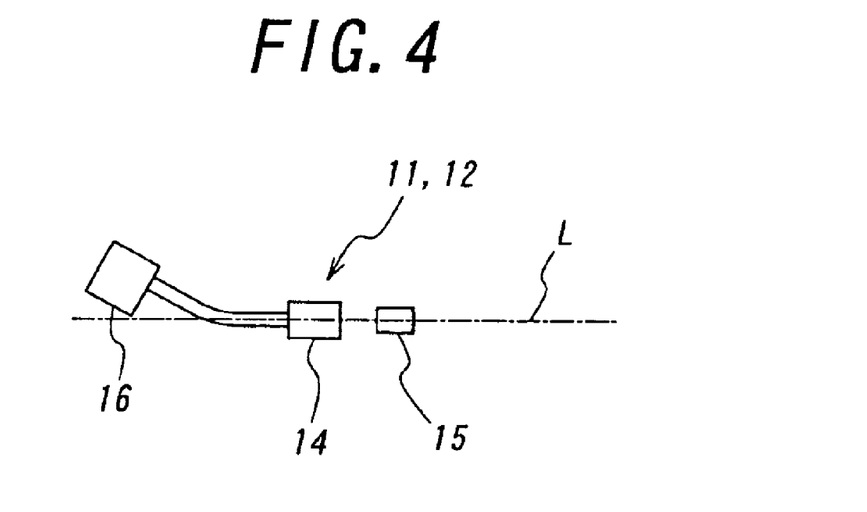
FIG. 4 is a configuration view showing a configuration of the tangential and vertical displacement sensor bodies.

FIG. 4 is a configuration view showing the configuration of the tangential displacement sensor body 11 and the vertical displacement sensor body 12. These sensor bodies 11 and 12 are composed of a bar magnet 15, a hall element probe 14 oppositely disposed on an axial line L of the bar magnet 15, and an amplifier 16. These sensor bodies 11 and 12 can detect changes in a gap between the tip of bar magnet 15 and the tip of the hall element probe 14 along the axial line.

Four bar magnets 15 constituting the four tangential displacement sensor bodies 11 are attached on the rim 2 to positions being symmetric with respect to the axial center of the rim 2. Four hall element probes 14 each corresponding to respective bar magnet 15 are attached on the disk 4 to positions being symmetric with respect to the axial center of the disk 4. The axial line L is directed to the tangential line.

In this state, each pair composed of the tip of the bar magnet 15 and the tip of the corresponding hall element probe 14 constitutes a paired corresponding point. Tangential relative displacements of these corresponding points are measured and the relative displacements of these four pairs are summed. A tangential displacement of the disk 4 with respect to the rim 2 is calculated based on the summed value $Y_1$. That is, when a continuously-changing rotation angle of the wheel 1, a distance from the axial center of the corresponding points, an amount of eccentricity, and the tangential relative displacement between the rim 2 and the disk 4 are designated as θ, r, D, and α, respectively, the tangential relative displacement α can be calculated from the summed value $Y_1$ of the four pairs of the relative displacements according to the above-mentioned equation (6). The value Y1 is independent from the continuously-changing rotation angle θ, so that the tangential relative displacement a can be real-timely calculated.

Figure 5:
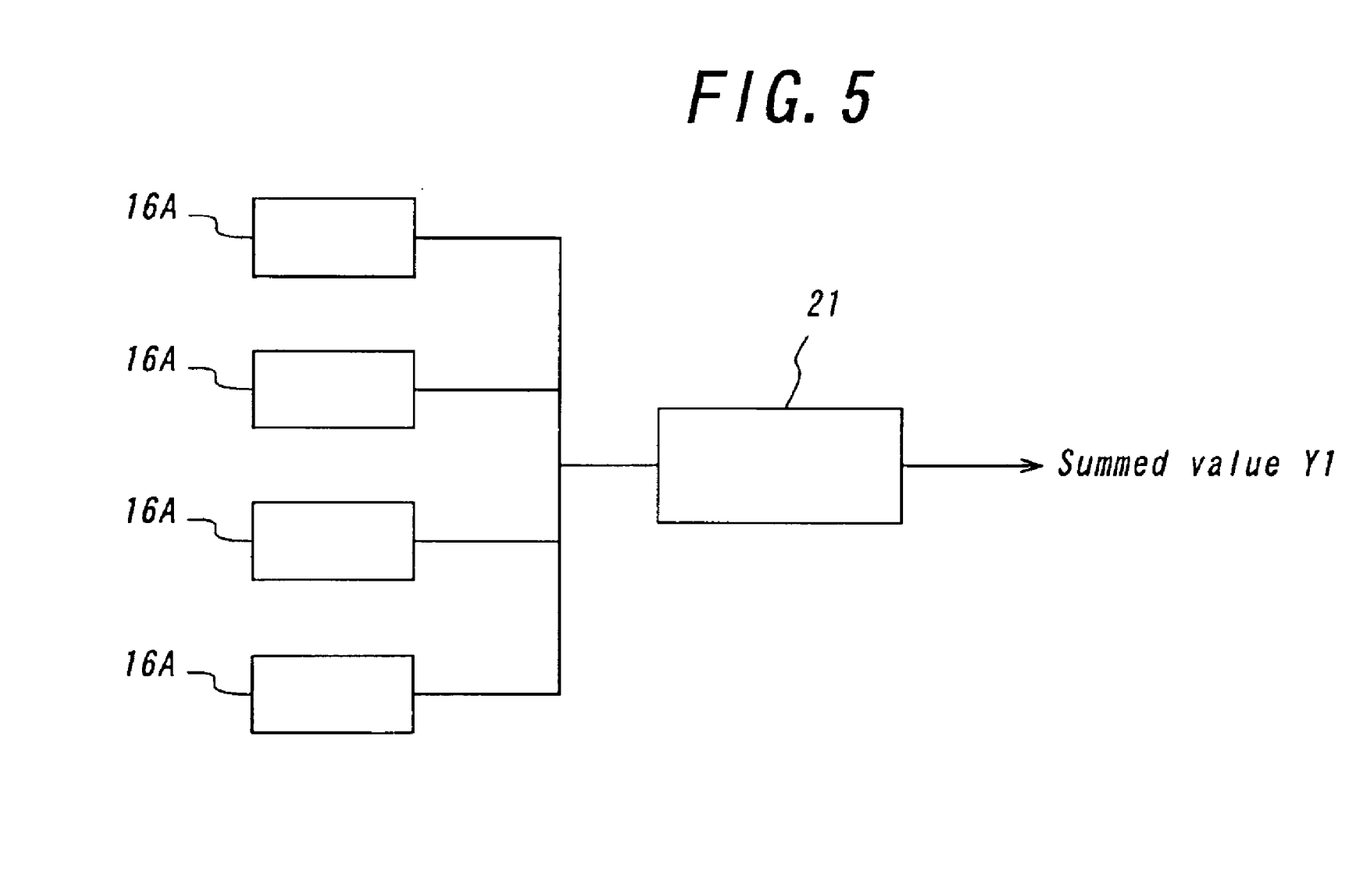
FIG. 5 is a block diagram of the circuit for computing the output of the tangential displacement sensor body.

FIG. 5 is a block diagram of a circuit for computing an output of the tangential displacement sensor body 11. The outputs of amplifiers 16A of the tangential displacement sensor body 11 are input to an accumulator 21 to output a summed value $Y_1$.

In the next, a method of calculating a vertical displacement with respect to the disk 4 of the rim 2, i.e. an amount of eccentricity is described. Four bar magnets 15 constituting the four vertical displacement sensor bodies 12 are attached on the rim 2 to positions being symmetric with respect to the axial center of the rim 2. Four hall element probes 14 each corresponding to the respective bar magnets 15 are attached on the disk 4 to positions being symmetric with respect to the axial center of the disk 4. The axial line L is directed to the radial direction.

In this state, each pair composed of the tip of the bar magnet 15 and the tip of the corresponding hall element probe 14 constitutes a paired corresponding point. Radial relative displacements of these corresponding points are measured and the products of two pairs of the relative displacements in diagonal relationships among the relative displacement are calculated. The two pairs of the products are summed to calculate the amount of eccentricity based on the summed value $Y_2$. That is, when a continuously-changing rotation angle of the wheel 1 and the amount of eccentricity are designated as θ and D, respectively, the amount of eccentricity D can be calculated from the summed value $Y_2$ according to the above-mentioned equation (6). The value $Y_2$ does not depend on the continuously-changing rotation angle θ, so that that the amount of eccentricity D can be real-timely calculated as an amount independent from the rotation angle θ.

Figure 6:
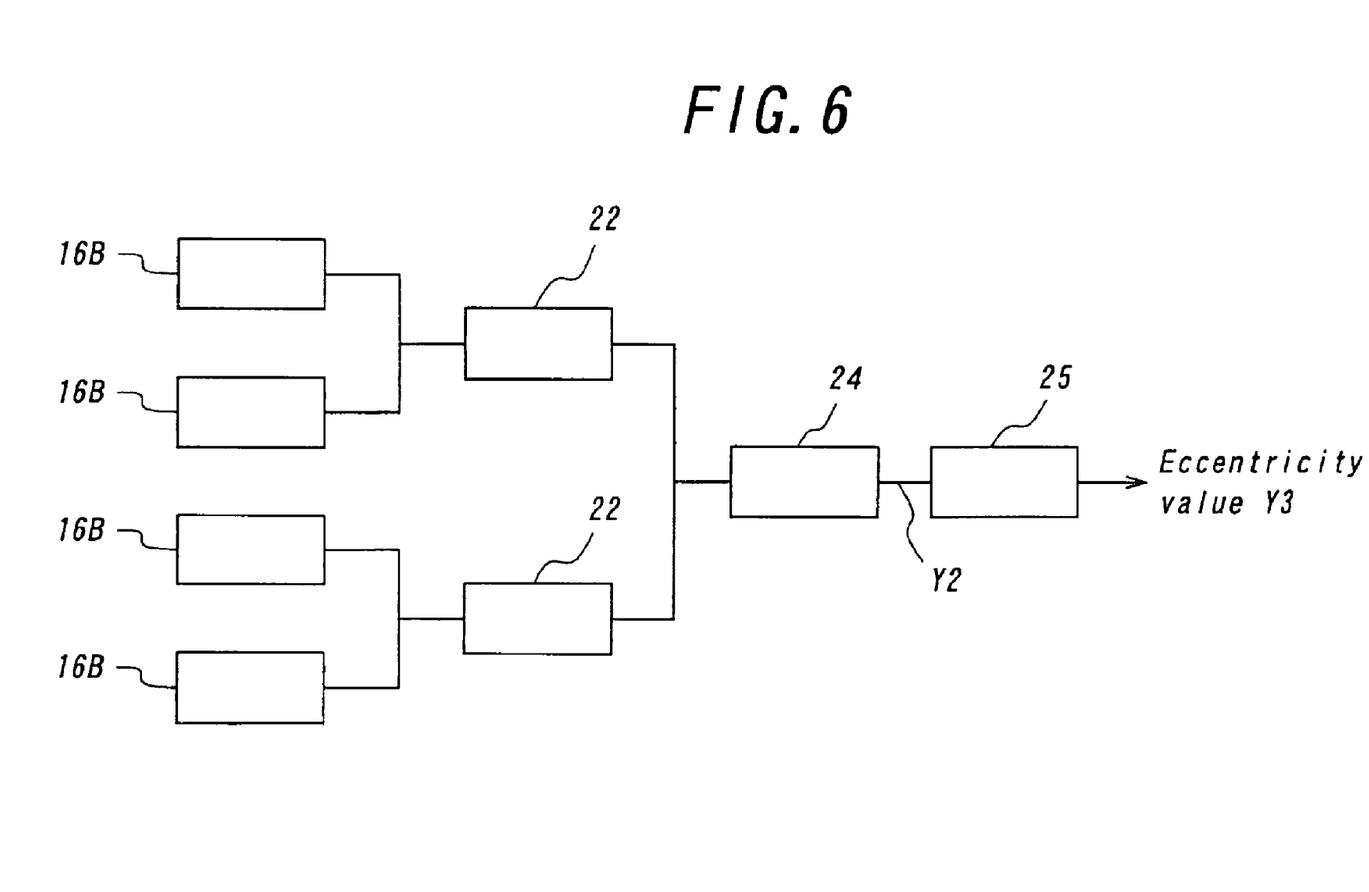
FIG. 6 is a block diagram of the circuit for computing the output of the vertical displacement sensor body.

FIG. 6 is a block diagram of a circuit for computing an output of the vertical displacement sensor body 12. The outputs from two multiplier for multiplying the outputs of the amplifiers 16B of the vertical displacement sensor bodies 12 diagonally displaced each other are summed by the accumulator 24 to out put as $Y_2$. $Y_2$ is computed by a software section 25 to inversely calculate a eccentricity value $Y_3$ corresponding to the amount of eccentricity D according to the equation (8).

Figure 7:
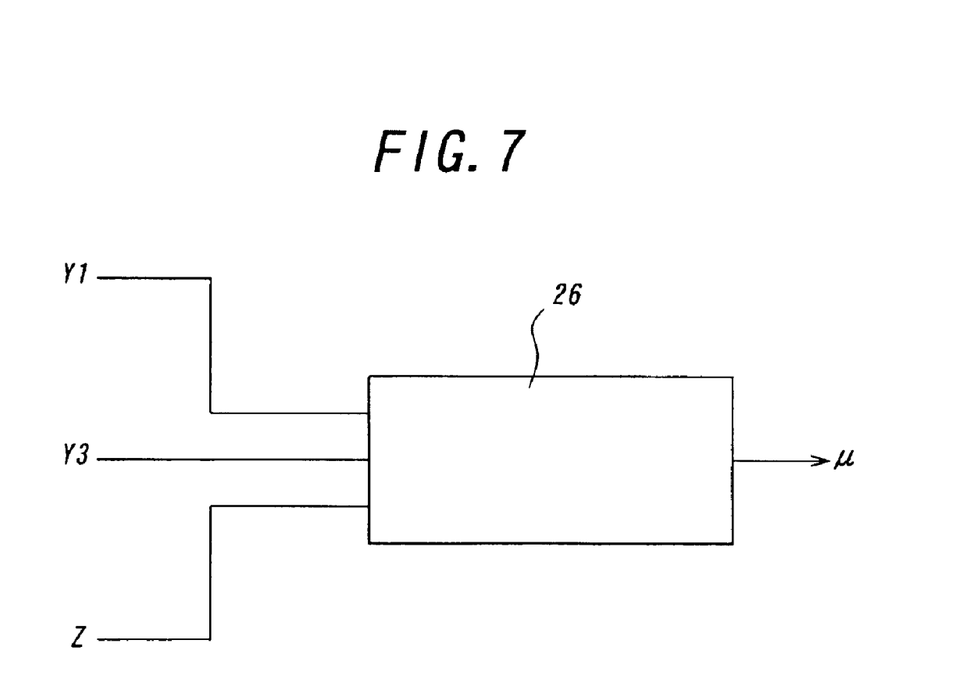
FIG. 7 is a block diagram showing the friction coefficient computing section.

FIG. 7 is a block diagram showing a friction coefficient-computing section 26 for calculating the friction coefficient. The friction coefficient-computing section 26 estimates and calculates the friction coefficient based on the summed value $Y_1$ from the tangential displacement sensor body 11, the amount of eccentricity $Y_3$ from the vertical displacement sensor body 12, and an input value Z of angular rate from a not-shown rotational speed sensor of the tire/wheel assembly according to the method of the above-mentioned equation (1).

The method of estimating the friction coefficient based on the output of each displacement sensor body has been described in the above with reference to the block diagrams shown in FIGS. 5–7. The amplifiers 16A and 16B of each displacement sensor body, accumulators 21 and 24 constituting the computing circuits for calculating the summed values $Y_1$ and $Y_2$, and the multiplier 22 are attached to each of the rotating tire/wheel assemblies and a computer section for calculating the friction coefficient from the summed values $Y_1$ and $Y_2$, i.e. the software section 25 and the friction coefficient-computing section 26 are equipped on the vehicle body side, so that the summed values $Y_1$ and $Y_2$ have to be transmitted from the tire/wheel assembly side to the vehicle body side, which is preferably not by means of signal lines. Because a wired transmission can transmit the signals via an slip ring or the like but it cannot avoid problems resulting from a wear or a heat due to a slip between the rotating section and the fixed section.

When the transmission is not by means of signal lines, it is wasteful to provide two transmission paths and transmit the summed values $Y_1$ and $Y_2$ from the tire/wheel assembly side to the vehicle body side by the paths, so that a multiplex transmission is preferable. Although transmitting signals by means of a radio wave is a common method among the methods not by means of signal lines, such a signal transmission from the tire/wheel assembly side to the vehicle body side of the running vehicle tends to be affected by a noise, so that a system of transmitting a signal by an electromagnetic induction is adopted.

Figure 8:
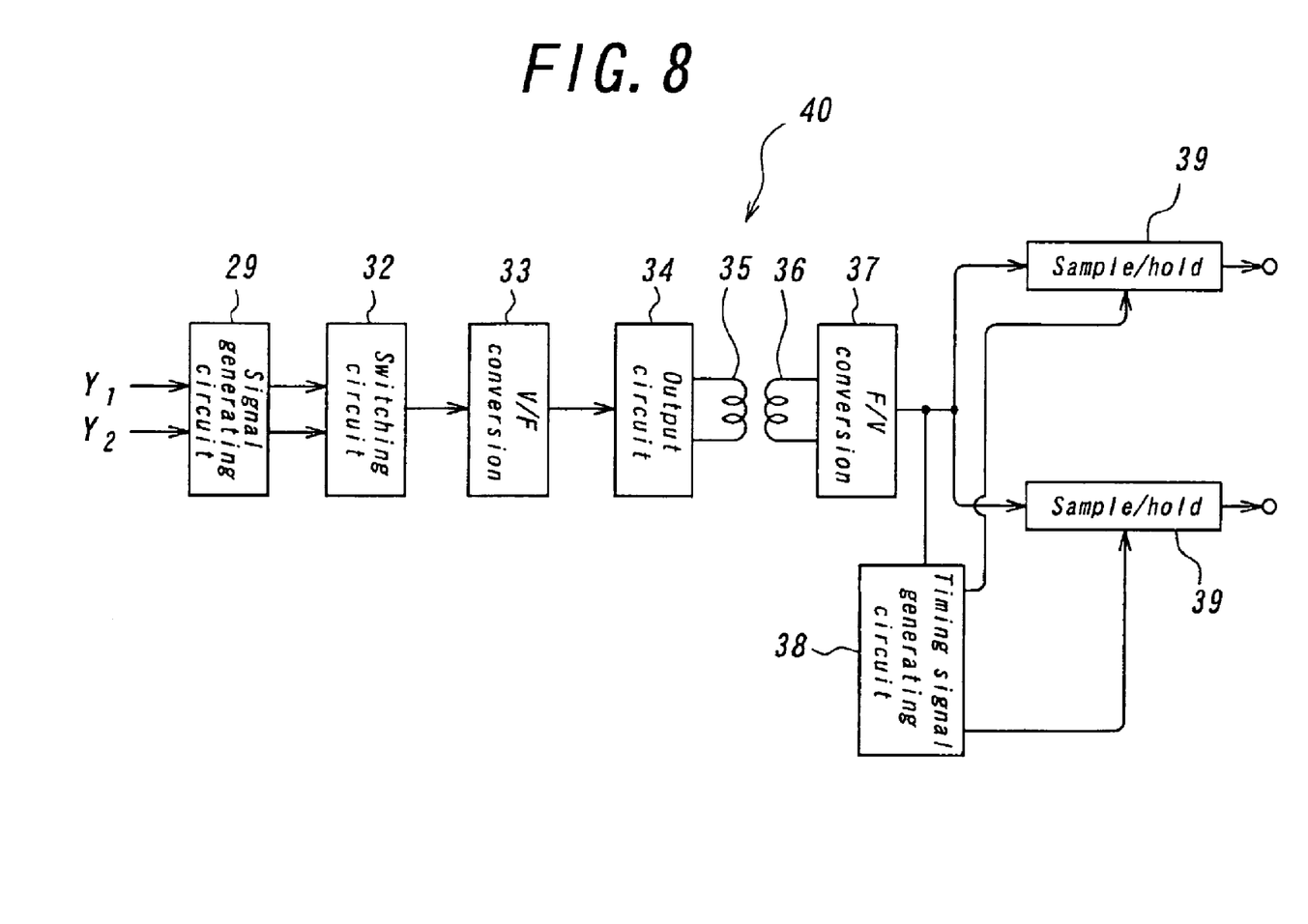
FIG. 8 is a block diagram showing the whole configuration of the signal multiple signal transmitting device.
Figure 9:
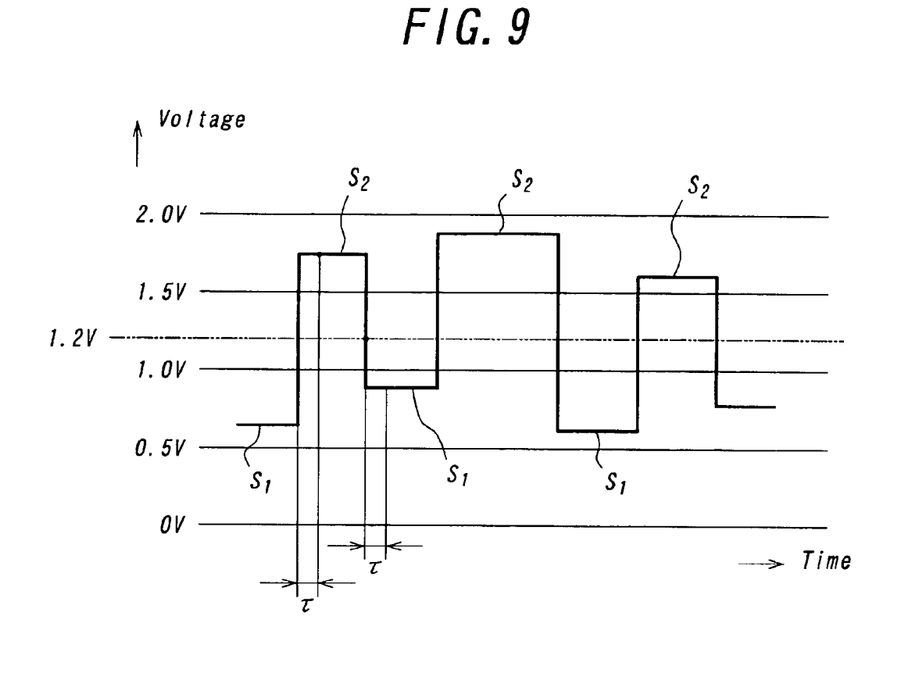
FIG. 9 is a signal wave form chart for explaining the generation of the timing signals.

With reference to FIGS. 8 and 9, a multiplex transmitting device used in this embodiment is described below. FIG. 8 is a block diagram showing a whole configuration of the multiplex transmitting device 40. The multiplex transmitting device 40 transmits the summed value signals $Y_1$ and $Y_2$ from the tire/wheel assembly side to the vehicle body side. The method of transmitting signals from the tire/wheel assembly side to the vehicle body side is discussed below. Original signals consisting of the summed values $Y_1$ and $Y_2$ are input to a signal generating circuit 29 and are converted at the signal generating circuit 29 without overlapping dynamic ranges with each over. As an example of the dynamic range, for example, the summed values $Y_1$ are in the voltage range of 0.5–1.0 V and $Y_2$ are in voltage ranges of 1.5–2.0V.

Then, the converted summed value signals are supplied to a switching circuit 32 and the switching circuit 32 sequentially switches and outputs the signals at a given cycle. In this specification, such a signal output from the switching circuit 32 is referred to as a "composite signal". As the dynamic ranges of the summed value signals $Y_1$ and $Y_2$ are different from each other, the signal jumps at the time of switching by the switching circuit 32.

The composite signal output from the switching circuit 32 in this manner is then supplied to a voltage-frequency conversion circuit 33. The voltage-frequency conversion circuit 33 has a function of converting the input signal to the output signal with the frequency corresponding the voltage, so that the voltage-frequency conversion circuit 33 outputs the composite signals with their frequency ranges being sequentially changed. Further, after the composite signals output from the voltage-frequency conversion circuit 33 are amplified by the output circuit 34, the amplified composite signal output from the output circuit 34 is supplied to a transmitting coil 35. The transmitting coil 35 is displaced to be concentric with the axle hub 7 and rotates integrally with the tire 6 and the wheel 1.

On the vehicle body side of the vehicle, a receiving coil 36 is disposed to face the above-mentioned transmitting coil 35 and is configured to receive the composite signals transmitted by the electromagnetic induction from the transmitting coil 35. As mentioned above, the amplifiers 16A and 16B of each displacement sensor body, the computing circuit including the accumulators 22 and 24, and multiplier 23, the switching circuit 32, the voltage-frequency conversion circuit 33, and the output circuit 34 as well as the transmitting coil 35 are disposed on the tire/wheel assembly side. Electric power for them is supplied by the electromagnetic induction from the receiving coil 36 to the transmitting coil 35, so that a power source such as a battery is not needed. As supplying electric power by the electromagnetic induction of the coil is known per se, no further detail is discussed here.

As mentioned above, the composite signal received by the receiving coil 36 is supplied to the frequency/voltage conversion circuit 37 to convert it to a composite signal having an amplitude corresponding to the frequency. The composite signal output from the frequency/voltage conversion circuit 37 contains mixed information of multiple signals, so that the signals need to be identified. To this end, the composite signal output from the frequency/voltage conversion circuit 37 is supplied to a timing signal generating circuit 38. The timing signal generating circuit 38 sets a plurality of given voltage levels as the thresholds. As shown in FIG. 9, the voltage at each boundary of the dynamic ranges, e.g. 1.2 V is set as the threshold.

In the case where the first signal $S_1$ in the composite signal switches to the second signal, the amplitude of the composite signal goes across the threshold of 1.2 V, and in the case where the second signal $S_2$ in the composite signal switches to the first signal, the amplitude of the composite signal goes across inversely (from the larger region to the smaller region). In this way, the amplitude of the composite signal goes across sequential thresholds at the switching of the sequential signals contained in the composite signal, so that the given signal can be appropriately sampled and held by sampling the signal at a time of the given time τ having passed since each of the timing signals was generated from the timing signal generating circuit 38 at these timing.

In this manner, the plurality of the timing signals output form the timing signal generating circuit 38 are respectively supplied to two sample/hold circuits 39 each receiving the composite signal output from the above-mentioned frequency/voltage conversion circuit 37. In these sample/hold circuit, the composite signal is sampled and held according to the sampling signals generated at a time of the time X having passed since each of the timing signals has generated, so that each of the original signals contained in the composite signal can be reproduced. In this way, a plurality of signals can be multiplex by the electromagnetic induction with the transmitting coil 35 and receiving coil 36. These signals are supplied to a signal processing circuit equipped in the vehicle body side where a given process is conducted to be able to estimate the friction coefficient.

In the above, a description is made to a case where the accumulators 21, 24 and the multiplier 22 are equipped on the rotating tire/wheel assembly. However, the accumulator 21, 24 and the multiplier 24 may be equipped on the vehicle body side. In this case, total of eight signals from the amplifiers 16A, 16B are input to the signal generating circuit 29 and the eight kinds of signals are converted into eight signals having dynamic ranges different from each other. Thereafter, the signals are transmitted to the vehicle body side as mentioned above to reproduce the eight original signals.

Moreover, as mentioned above, in the method and device of multiplex transmission of the signals according to the present invention, operations similar to the sampling of each signal are conducted at the switching circuit 22, so that a switching frequency in the switching circuit 22 can be determined based on the sampling theorem. For example, when the highest frequency in a plurality of the signals to be transmitted and the number of the signals are designated as $f_H$ and N, respectively, and each signal is transmitted at the same rate, the switching frequency $f_S$ may be $f_S=2Nf_H$.

Further, the present invention is not limited to the above-mentioned examples, there may be a number of modifications and variations. For example, in the above-mentioned example, the contiguous dynamic ranges of a plurality of the signals to be transmitted are set, but discontiguous dynamic ranges such as 0–1 V for the first signal and 2–3V for the second signal may be set. Also, in the above-mentioned example, all the transmitting rate of the signals are set to be equal by sequentially transmitting a plurality of the signals, but the transmitting rate of each signal may be varied.

INDUSTRIAL APPLICABILITY

As having been clearly shown in the above description, according to the present invention, the tangential and vertical forces acting on the elastic body on the elastic wheel are measured and the friction coefficient of the road surface is estimated based on the measured forces, so that the friction coefficient of the road surface can be directly and accurately estimated while being independent from the slip rate, which contributing an improvement in a performance of the ABS.

Moreover, when the measured values measured at the tire/wheel assembly side are transmitted to the ABS on the vehicle body side, a plurality of signals are multiplexed and transmitted by the action of electromagnetic induction. Thus, a transmitting device being simple and highly tolerant of noises can be configured. In addition, by multiplexing the signals, the ABS capable of transmitting a number of information within a given time and having a short response time can be realized.

Further, the method and device of multiplex transmission of signals are applicable not only for the transmission between the rotating tire/wheel assembly and the vehicle body, but also for other application of transmitting a number of signals without using signal lines.

What is claimed is:

1. A method for estimating friction coefficient of a road surface, comprising calculating, in a tire/wheel assembly having an axle hub, a tire, and a wheel attached to the axial hub to support the tire, tangential and vertical components of a force acting between a section of a transmission path between the axle hub and the tire and the other section of the transmission path based on measurement values of relative displacements in the tangential and vertical directions, respectively, between the sections of the transmission path, the sections of the transmission path being bounded by an elastic body arranged within the transmission path; and in order to calculate the friction coefficient between the tire/wheel assembly and the road surface based on the acting force of these components, measuring an angular rate of the tire/wheel assembly along with measurements of each component of the acting force, and calculating the friction coefficient μ between the tire/wheel assembly and the road surface from the equation $\mu=(Fb+(I_0/R)d\omega/dt)/N$, with the measured tangential force Fb, vertical force N and angular rate co as well as the known moment of inertia $I_0$ and known effective radius R of the tire/wheel assembly.

2. The method for estimating friction coefficient of a road surface according to claim 1, wherein the tangential relative displacements are summed among each of four pairs of points comprising four points symmetrically arranged on said section of the transmission path about its axial center and, associated with these points, four corresponding points symmetrically arranged on said the other section of the transmission path about its axial center, and the tangential relative displacement of said section and said the other section of the transmission path is determined based on the summed value.

3. The method for estimating friction coefficient of a road surface according to claim 1, wherein the radial relative displacements are measured among each of four pairs of points comprising four points symmetrically arranged on said section of the transmission path about its axial center and, associated with these points, four corresponding points symmetrically arranged on said the other section of the transmission path about its axial center, the products of two pairs of the relative displacements in a diagonal relation among the relative displacement are respectively calculated and summed, and the vertical relative displacement of said section and said the other section of the transmission path is determined based on the summed value.

4. The method for estimating friction coefficient of a road surface according to claim 1, wherein a hall element is used to measure a change in magnetic flux density of a magnetic body, and the tangential or radial relative displacement is detected based on the amount of the change.

5. A method of a multiplex transmission of signals, characterized in that, upon transmitting signals of the measured values recited in claim 1, or other signals, between the vehicle body side and the rotating tire/wheel assembly side, a composite signal obtained by a voltage/frequency conversion of a plurality of signals is supplied to a transmitting coil while switching the signals to transmit to a receiving coil by an electromagnetic induction, said plurality of signals having dynamic ranges without overlapping with each other, a plurality of signals obtained by a frequency/voltage conversion of the composite signal received by the receiving coil is processed to generate timing signals with a plurality of given voltage levels as thresholds, and said composite signal obtained by the frequency/voltage conversion is sampled according to said timing signals to reproduce a plurality of the original signals.

6. A device of multiplex transmission of signals for carrying out the method of multiplex transmission of signals according to claim 5, comprising:

a signal-generating circuit for generating a plurality of signals having dynamic ranges without overlapping with each other; a switching circuit for outputting a composite signal by sequentially switching the plurality of signals simultaneously output from the signal-generating circuit at a given cycle; a voltage/frequency conversion circuit for converting the composite signal output from the switching circuit into a composite signal having a frequency corresponding to the voltage; an output circuit for amplifying the composite signal output from the voltage/frequency conversion circuit; a transmitter coil for transmitting the amplified composite signal output from the output circuit; a receiver coil for receiving the composite signal transmitted from the transmitter coil by the action of electromagnetic induction; a frequency/voltage conversion circuit for converting the composite signal received by the receiver coil into a composite signal having an amplitude corresponding to the frequency; a timing signal-generating circuit for generating a plurality of timing signals by processing the composite signal output from the frequency/voltage conversion circuit with a plurality of given voltage levels as thresholds; a plurality of sample/hold circuits for sampling the composite signal output from the frequency/voltage conversion circuit according to the timing signals to reproduce a plurality of the original signals.

7. The method for estimating friction coefficient of a road surface according to claim 2, wherein a hall element is used to measure a change in magnetic flux density of a magnetic body, and the tangential or radial relative displacement is detected based on the amount of the change.

8. The method for estimating friction coefficient of a road surface according to claim 3, wherein a hall element is used to measure a change in magnetic flux density of a magnetic body, and the tangential or radial relative displacement is detected based on the amount of the change.

9. A method of a multiplex transmission of signals, characterized in that, upon transmitting signals of the measured values recited in claim 2, or other signals, between the vehicle body side and the rotating tire/wheel assembly side, a composite signal obtained by a voltage/frequency conversion of a plurality of signals is supplied to a transmitting coil while switching the signals to transmit to a receiving coil by an electromagnetic induction, said plurality of signals having dynamic ranges without overlapping with each other, a plurality of signals obtained by a frequency/voltage conversion of the composite signal received by the receiving coil is processed to generate timing signals with a plurality of given voltage levels as thresholds, and said composite signal obtained by the frequency/voltage conversion is sampled according to said timing signals to reproduce a plurality of the original signals.

10. A method of a multiplex transmission of signals, characterized in that, upon transmitting signals of the measured values recited in claim 3, or other signals, between the vehicle body side and the rotating tire/wheel assembly side, a composite signal obtained by a voltage/frequency conversion of a plurality of signals is supplied to a transmitting coil while switching the signals to transmit to a receiving coil by an electromagnetic induction, said plurality of signals having dynamic ranges without overlapping with each other, a plurality of signals obtained by a frequency/voltage conversion of the composite signal received by the receiving coil is processed to generate timing signals with a plurality of given voltage levels as thresholds, and said composite signal obtained by the frequency/voltage conversion is sampled according to said timing signals to reproduce a plurality of the original signals.

11. A method of a multiplex transmission of signals, characterized in that, upon transmitting signals of the measured values recited in claim 4, or other signals, between the vehicle body side and the rotating tire/wheel assembly side, a composite signal obtained by a voltage/frequency conversion of a plurality of signals is supplied to a transmitting coil while switching the signals to transmit to a receiving coil by an electromagnetic induction, said plurality of signals having dynamic ranges without overlapping with each other, a plurality of signals obtained by a frequency/voltage conversion of the composite signal received by the receiving coil is processed to generate timing signals with a plurality of given voltage levels as thresholds, and said composite signal obtained by the frequency/voltage conversion is sampled according to said timing signals to reproduce a plurality of the original signals.

* * * * *